(12) United States Patent
Horvitz et al.

(10) Patent No.: US 6,596,495 B1
(45) Date of Patent: Jul. 22, 2003

(54) **EGL-1, A NEW PROTEIN REQUIRED FOR PROGRAMMED CELL DEATH IN *C. ELEGANS* THAT INTERACTS WITH THE BCL-2-LIKE PROTEIN CED-9**

(75) Inventors: H. Robert Horvitz, Auburndale, MA (US); Barbara Conradt, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/087,137

(22) Filed: May 28, 1998

Related U.S. Application Data

(60) Provisional application No. 60/085,541, filed on May 15, 1998, and provisional application No. 60/047,836, filed on May 28, 1997.

(51) Int. Cl.[7] .......................... G01N 33/68; A61K 38/17; C07K 14/435
(52) U.S. Cl. ........................ 435/7.1; 436/501; 530/350; 514/2; 514/12
(58) Field of Search .......................... 530/350; 435/7.1; 436/501; 514/12, 2

(56) References Cited

PUBLICATIONS

Bowie et al. Deciphering the message in protein sequences: tolerance to amino acid substitutions. Science 247: 1306–1310, Mar. 16, 1990.*

Wells. Additivity of mutational effects in proteins. Biochemistry 29(37): 8509–8517, Mar. 16, 1990.*

Callard et all. The Cytokine FactsBook. New York: Academic Press., p. 31, 1994.*

Boyd, J.M. et al., "Bik, a novel death–inducing protein shares a distinct sequence motif with Bcl–2 family proteins and interacts with viral and cellular survival–promoting proteins", *Oncogene* 11:1921–1928, (1995).

Chen, F. et al., "Functional regulation of ced–4 subcellular localization in *C. elegans* by ced–9 and upstream cell–death activators", Early 1998 East Coast Worm Meeting abstract 33 (1998).

Chinnaiyan, A.M. et al., "Interaction of CED–4 with CED–3 and CED–9: a molecular framework for cell death", *Science* 275:1122–1126, (1997).

Chinnaiyan, A.M. et al., "Role of CED–4 in the activation of CED–3", *Nature* 388:728–729, (1997).

Chittenden, T. et al., "A conserved domain in Bak, distinct from BH1 and BH2, mediates cell death and protein binding functions", *EMBO J.* 14:5589–5596, (1995).

Conradt, B. et al., "Towards the cloning of egl–1, which can mutate to cause the HSNs to undergo programmed cell death", 1995 International Worm Meeting abstract 162 (1995).

Conradt, B. et al., "Revertants of the egl–1 phenotype reveal a new gene required for programmed cell death in *C. elegans*", 1996 East Coast Worm Meeting abstract 123 (1996).

Conradt, B. et al., "A new gene required for programmed cell death in *C. elegans* revealed by reverting the EGL–1 (gf) phenotype", 1996 European Worm Meeting Abstract 17 (1996).

Conradt, B. et al., "ced(n3082) V, a gene that can mutate to block programmed cell death in *C. elegans*", Early 1997 International Worm Meeting abstract 98 (1997).

Conradt, B. et al., "egl–1 is required for programmed cell death and encodes a BH3–containing protein", Early 1998 East Coast Worm Meeting Abstract 37 (1998).

Conradt, B. et al., "egl–1 is required for programmed cell death in the soma and encodes a BH3–containing protein that interacts with ced–9", Early 1998 European Worm Meeting Abstract 20 (1998).

Conradt, B. et al., "The *C. elegans* protein EGL–1 is required for programmed cell death and interacts with the Bcl–2–like protein CED–9", *Cell* 94:519–529, (1998).

Desai, C. and Horvitz, H.R., "*Caenorhabditis elegans* mutants defective in the functioning of the motor neurons responsible for egg laying", *Genetics* 121:703–721, (1989).

Diaz, J.–L. et al., "A common binding site mediates heterodimerization and homodimerization of Bcl–2 family members", *J. Biol. Chem.*, 272:11350–11355, (1997).

Ellis, H.M. and Horvitz, H.R., "Genetic control of programmed cell death in the nematode *C. elegans*", *Cell* 44:817–829, (1986).

Ellis, R.E. and Horvitz, H.R., "Two *C. elegans* genes control the programmed deaths of specific cells in the pharynx", *Development* 112:591–603, (1991).

Ellis, R.E. et al., "Mechanisms and functions of cell death", *Annu. Rev. Cell Biol.* 7:663–698, (1991).

Fraser, A. and Evan, G. "A license to kill", *Cell* 85:781–784, (1996).

Han, J. et al., "Induction of apoptosis by human Nbk/Bik, a BH3–containing protein that interacts with E1B 19K", *Mol. Cell. Biol.* 16:5857–5864, (1996).

Han, J. et al., "The E1B 19K protein blocks apoptosis by interacting with and inhibiting the p53–inducible and death-–promoting Bax protein", *Genes Dev.* 10:461–477, (1996).

Hengartner, M.O. and Horvitz, H.R., "Activation of *C. elegans* cell death protein CED–9 by an amino–acid substitution in a domain conserved in Bcl–2", *Nature* 369:318–320, (1994).

(List continued on next page.)

Primary Examiner—Gabrielle Bugaisky
(74) Attorney, Agent, or Firm—Clark & Elbing LLP; Kristina Bieker-Brady

(57) ABSTRACT

The invention provides a novel protein, EGL-1, involved in cell death and methods for identifying compounds and genes which affect the cell death pathway.

15 Claims, 18 Drawing Sheets

OTHER PUBLICATIONS

Hengartner, M.O. and Horvitz, H.R., "*C. elegans* cell survival gene ced–9 encodes a functional homolog of the mammalian proto–oncogene bcl–2", *Cell* 76:665–676, (1994).

Hengartner, M.O. et al., "*Caenorhabditis elegans* gene ced–9 protects cells from programmed cell death", *Nature* 356:494–499, (1992).

Horvitz, H. R. et al., "The genetics of programmed cell death in the nematode *Caenorhabditis elegans*", *Cold Spring Harbor Symposia on Quantitative Biology LIX*, pp. 377–385, (1994).

Hunter, J.J. et al., "Functional dissection of the human Bcl–2 protein: sequence requirements for inhibition of apoptosis", *Mol. Cell. Biol.* 16:877–883, (1996).

Hunter, J.J. and Parslow, T.G., "A peptide sequence from Bax that converts Bcl–2 into an activator of apoptosis", *J. Biol. Chem.* 271:8521–8524, (1996).

Inohara, N. et al., "Harakiri, a novel regulator of cell death, encodes a protein that activates apoptosis and interacts selectively with survival–promoting proteins Bcl–2 and Bcl–$X_L$", *EMBO J.* 16:1686–1694, (1997).

Jacobson, M.D., "Programmed cell death: a missing link is found", *Trends Cell Biol.* 7:467–469, (1997).

James, C. et al., "CED–4 induces chromatin condensation in *Schizosaccharomyces pombe* and is inhibited by direct physical association with CED–9", *Curr. Biol.* 7:246–252, (1997).

Kelekar, A. et al., "Bad is a BH3 domain–containing protein that forms an inactivating dimer with Bcl–$x_L$", *Mol. Cell. Biol.* 17:7040–7046, (1997).

Metzstein, M. et al., "Transcriptional regulator of programmed cell death encoded by *Caenorhabditis elegans* gene ces–2.", *Nature* 328:545–547 (1996).

Muchmore S.W. et al., "X–ray and NMR structure of human bcl–$x_L$, an inhibitor of programmed cell death", *Nature* 381:335–341, (1996).

Nicholson, D.W. and Thornberry, N.A., "Caspases: killer proteases", *Trends Biochem. Sci.* 22:299–306, (1997).

Ottilie. S. et al., "Dimerization properties of human Bad", *J. Biol. Chem.* 272:30866–30872, (1997).

Ottilie, S., et al., "Mutational analysis of the interacting cell death regulators CED–9 and CED–4", *Cell Death and Differentiation* 4:526–533, (1997).

Raff, M.C., "Social controls on cell survival and cell death", *Nature* 356:397–400, (1992).

Rinkenberger, J.L. and Korsmeyer, S. J. "Errors of homeostasis and deregulated apoptosis", *Curr. Op. Gen. Dev.* 7:589–596, (1997).

Sattler, M. et al., "Structure of Bcl–$x_L$–Bak peptide complex: recognition between regulators of apoptosis", *Science* 275:983–986, (1997).

Seshagiri, S. et al.,"*Caenorhabditis elegans* CED–4 stimulates CED–3 processing and CED–3–induced apoptosis", *Curr. Biol.* 7:455–460, (1997).

Shaham, S. and Horvitz, H. R. "Developing *Caenorhabditis elegans* neurons may contain both cell–death protective and killer activities", *Genes Dev.* 10:578–591, (1996).

Shaham, S. and Horvitz, H. R. "Alternatively spliced *C. elegans* ced–4 RNA encodes a novel cell–death inhibitor", *Cell* 86:201–208, (1996).

Spector, M. S., et al., "Interactions between the *C. elegans* cell–death regulators CED–9 and CED–4", *Nature* 385:653–656, (1997).

Trent, C., et al., "Egg–laying defective mutants of the nematode *Caenorhabditis elegans*", *Genetics* 104:619–647, (1983).

Vaux, D.L., "CED–4–The third horseman of apoptosis", *Cell* 90:389–390, (1997).

Wang, K. et al., "Bid: a novel BH3 domain–only death agonist", *Genes Dev.* 10:2859–2869, (1996).

Wild, Direct Submission. LOCUS: CEF23B12, ENTREZ Document retrieval System, Release 24.0, National Center for Biotechnology Information, National Library of Medicine, National Institute of Health ISSN 1078–7712 (1996).

Williams et al., "A Genetic Mapping System in *Caenorhabditis elegans* Based on Polymorphic Sequence–Tagged Sites", *Genetics* 131:609–614 (1992).

Wilson et al., "2.2 Mb of contiguous nucleotide sequence from chromosome III of *C. elegans*", *Nature* 368:32–38 (1994).

White, E., "Life, death, and the pursuit of apoptosis", *Genes Dev.* 10:1–15, (1996).

Wu, D. et al., "Interaction and regulation of subcellular localization of CED–4 and CED–9", *Science.* 275:1126–1129, (1997).

Wu, D. et al., "Interaction and regulation of the *Caenorhabditis elegans* death protease CED–3 by CED–4 and CED–9", *J. Biol. Chem.* 272:21449–21454 (1997).

Xue, D. and Horvitz, H.R., "*Caenorhabditis elegans* CED–9 protein is a bifunctional cell–death activator", *Nature* 390:305–308 (1997).

Yin, X,–M. et al., "BH1 and BH2 domains of Bcl–2 are required for inhibition of apoptosis and heterodimerization with Bax", *Nature* 369:321–323 (1994).

Zarkower, D. and Hodgkin, J. "Molecular analysis of the *C. elegans* sex–determining gene tra–1: a gene encoding two zinc finger proteins", *Cell* 70:237–249 (1992).

Zha, H. et al., "Proapoptotic protein Bax heterodimerizes with Bcl–2 and homodimerizes with Bax via a novel domain (BH3) distinct from BH1 and BH2", *J. Biol. Chem.* 271:7440–7444 (1996).

Zha, J. et al., "BH3 domain of Bad is required for heterodimerization with Bcl–$X_L$ and proapoptotic activity", *J. Biol. Chem.* 272:24101–24104, (1997).

\* cited by examiner

**Screen for Revertants of the *egl-1(gf)* Phenotype**

I) Genetic Screen Using the *egl-1(gf)* allele *n1084*

Pick rare non-Egl F1 animals

II) Seven Mutations, Representing One Complementation Group, Can Revert the *egl-1(gf)* Phenotype

Characterization of the Revertant egl-1(n1084 n3082)

1) n3082 Suppresses the egl-1(n1084) Phenotype by Suppressing the Death of the HSNs

| Strain | % Egl Animals | % HSNs Present |
|---|---|---|
| N2 | 1 (n=248) | 100 (n=10) |
| egl-1(n1084) | 99 (n=166) | 0 (n=20) |
| egl-1(n1084 n3082) | 0 (n=113) | 78 (n=25) |

Fig. 3

II) n3082 Suppresses the Death of not only the HSNs but Most if not All Cells Normally Undergoing Programmed Cell Death and therefore causes a "Ced" Phenotype

| Strain | # of Extra Cells in Anterior Pharynx (+SD), n=15 |
|---|---|
| N2 | 0.0 ± 0.0 |
| egl-1(n1084) | 0.1 ± 0.3 |
| egl-1(n1084 n3082) | 11.1 ± 2.5 |
| egl-1(n1084 n3082)/+ | 0.1 ± 0.3 |
| egl-1(n1084 n3082)/nDf42 | 11.5 ± 1.5 |
| ced-3(n717) | 10.7 ± 1.7 |
| ced-4(n1162) | 10.2 ± 1.5 |
| ced-9(n1950) | 12.4 ± 1.9 |

Fig. 4

Transformation Rescue of *n3082*'s Ced Phenotype

| Cosmid Pool | Rescue (Corpses in Embryos) |
|---|---|
| A | - |
| B | - |
| C | + |

*egl-1* Transcript

```
5' A TTC ACA CCC AAA ACA TTC ACA CCG ATT AGT CGT ATT CTA ACT TCT CTT T    50

TC AAT TCA GTT GAT ATG CTG ATG CTC ACC TTT GCC TCA ACC TCT TCG GAT    100

CTT CTA CCA ATG TCC AAC GTT TTT GAC GTT CAA TCT TCC GTT TTC TAC AA    150
                M   S   N   V   F   D   V   Q   S   S   V   F   Y   N
    C GAA AAG AAC ATG TTC TAC TCC TCG TCT CAG GAC TTC TCC TCG TGT GAA G   200
      E   K   N   M   F   Y   S   S   S   Q   D   F   S   S   C   E   D
    AT TCT TCT CAA TTT GCC GAC GAC TCG GGA TTT TTT GAT GAC TCT GAG ATC    250
       S   S   Q   F   A   D   D   S   G   F   F   D   D   S   E   I
    AGC AGC ATC GGC TAC GAG ATC GGC TCC AAG CTA GCA GCA ATG TGC GAT GA    300
     S   S   I   G   Y   E   I   G   S   K   L   A   A   M   C   D   D
    C TTC GAT GCT CAG ATG ATG TCC TAC TCG GCC CAT GCT TCC GAC AGA AGC C   350
       F   D   A   Q   M   M   S   Y   S   A   H   A   S   D   R   S   L
    TC TTC CAT CGT CTT CTG GAC TTT TTC GCT TTT TAA GTG ATC AAA ATC TCC    400
        F   H   R   L   L   D   F   F   A   F
    AAC TTT TCT CCA ATT TGT ACC ATG ATT TCT CAT AAT ACC CGG TGT TTT TT    450

C TTC ATT TGT GAT TAT TTT TCG ATC TCT CCG TCT CCA ACT CCC CTC AAT A   500

TT TGT ACC ATA GTC CTT TAT TGC TCA TAT TTA TCT AAT AAT AAA TAT GGT    550

TTT TTT TAA    3'                                                     559
```

Fig. 7

```
ATTCACACCCAAAAACATTCACACCGATTAGTCGTATTCTAACTTCTCTTTCAATTCAGTTGATATGCTGATGCTCACCTTTGCCTCAAC        90

CTCTTCGGATCTTCTACCAATGTCCAACGTTTTTGACGTTCAATCTTCCGTTTTCTACAACGAAAAGAACATGTTCTACTCCTCGTCTCA       180
   M  S  N  V  F  D  V  Q  S  S  V  F  Y  N  E  K  N  M  F  Y  S  S  S  Q                          24
                                                       n3082
GGACTTCTCCTCGTGTGAAGATTCTTCTCAATTGCCGACGACTCGGGATTTTTGATGACTCTGAGATCAGCAGCATCGGCTACGAGAT         270
 D  F  S  S  C  E  D  S  S  Q  F  A  D  D  S  G  F  F  D  D  S  E  I  S  S  I  G  Y  E  I         54

CGGCTCCAAGCTTAGCAGCAATGTGCGATGACTTCGATGCTCAGATGATGTCCTACTCGGGCCCATGCTTCCGACAGAAGCCTCTTCCATCG    360
 G  S  K  L  A  A  M  C  D  D  F  D  A  Q  M  M  S  Y  S  A  H  A  S  D  R  S  L  F  H  R         84

TCTTCTGGACTTTTTCGCTTTTTAAGTGATCAAAATCTCCAACTTTTCTCCAATTGTACCATGATTCTCATAATACCCGGTGTTTTT         450
 L  L  D  F  F  A  F                                                                               91

CTTCATTTGTGATTATTTTCGATCTCTCCGCTCCCAACTCCCCCAATATTTGTACCATAGTCCTTTATTGCTCATATTTATCTAATAA         540

TAAATATGGTTTTTTTA(n)                                                                              557
```

Fig. 8A

| | | |
|---|---|---|
| EGL-1 | 58 | L A A M C D D F D 66 |
| hBik | 61 | L A C I G D E M D 69 |
| mBid | 90 | L A Q I G D E M D 98 |
| hHarakiri | 37 | L K A L G D E L H 45 |
| mBad | 151 | L R R M S D E F E 159 |
| hBak | 78 | L A I H I G D D I N 86 |
| hBax | 63 | L K R I G D E L D 71 |

Fig. 8B

Epistasis Analysis

I) n3082 Does Not Suppress the Lethality Caused by ced-9(lf) Mutations

| Strain | Viability |
|---|---|
| ced-9(lf) | - |
| ced-9(lf); ced-3(lf) | + |
| ced-4(lf) ced-9(lf) | + |
| ced-9(lf); egl-1(n1084 n3082) | - |

Fig. 11

II) n3082 Acts at Least Partly Through ced-9

| Strain | Viability | # of X-tra cells (n=15) |
|---|---|---|
| ced-9(n2812) | − | 0.0 |
| ced-3(n2427) | + | 1.6 |
| ced-9(n2812); ced-3(n2427) | + | 6.3 |
| egl-1(n1084 n3082) | + | 11.1 |
| ced-3(n2427); egl-1(n1084 n3082) | + | 11.1 |
| ced-9(n2812); ced-3(n2427); egl-1(n1084 n3082) | + | 7.0 |

Fig. 12

III) *n3082* Can Suppress a *ces-1(lf)* Mutation

| Strain | Fate of NSM sister cell |
|---|---|
| *ces-1(lf)* | dies |
| *egl-1(n1084 n3082)* | survives |
| *ces-1(lf); egl-1(n1084 n3082)* | survives |

Fig. 13

OF CORPSES IN THE HEAD OF TRANSGENIC L1 ANIMALS

| Strain | Mock (n=15) | | Heatshocked (n=15) | |
|---|---|---|---|---|
| pHS vector alone | 0.5 | (0-2) | 0.4 | (0-2) |
| pHS/2 | 6.9 | (1-19) | 54.3 | (16-75)* |
| pHS/2; dpy-4 ced-3(n717) | 0.6 | (0-2) | 0.5 | (0-2) |
| pHS/2; dpy-4 ced-3(n717); outcrossed | 7.2 | (2-19) | 59.5 | (43-81)* |
| pHS/2; lon-1 ced-4(n1162) | 0.7 | (0-2) | 0.6 | (0-2) |
| pHS/2; sma-2 ced-9(n1195) | 0.5 | (0-1) | 1.3 | (0-4) |
| ced-1; unc-76 | 23.3 | (17-28) | N.D. | |
| ced-1; egl-1(n1084 n3082) unc-76 | 0.9 | (0-3) | N.D. | |

\* n=4 and 6

Strain injected: ced-1(e1735); egl-1(n1084) n3082 unc-76(e911)
Co-injection Marker: p76-16B

Fig. 18

SEQUENCE LISTING

<160> NUMBER OF SEQ ID NOS: 2

<210> SEQ ID NO 1
<211> LENGTH: 559
<212> TYPE: DNA
<213> ORGANISM: Caenorhabditis elagans

<400> SEQUENCE: 1

```
attcacaccc aaaacattca caccgattag tcgtattcta acttctcttt tcaattcagt      60
tgatatgctg atgctcacct ttgcctcaac ctcttcggat cttctaccaa tgtccaacgt     120 tttttgacgtt caatcttccg tttttctacaa cgaaaagaac atgttctact cctcgtctca   180
ggacttctcc tcgtgtgaag attcttctca atttgccgac gactcgggat tttttgatga    240
ctctgagatc agcagcatcg gctacgagat cggctccaag ctagcagcaa tgtgcgatga   300
```

-continued

```
cttcgatgct cagatgatgt cctactcggc ccatgcttcc gacagaagcc tcttccatcg      360
tcttctggac tttttcgctt tttaagtgat caaaatctcc aactttttctc caatttgtac     420 catgatttct cataataccc ggtgtttttt cttcatttgt gattattttt cgatctctcc      480
gtctccaact ccctcaata tttgtaccat agtcctttat tgctcatatt tatctaataa       540
taaatatggt ttttttttaa                                                  559
```

<210> SEQ ID NO 2
<211> LENGTH: 91
<212> TYPE: PRT
<213> ORGANISM: Caenorhabditis elagans

<400> SEQUENCE: 2

```
Met Ser Asn Val Phe Asp Val Gln Ser Ser Val Phe Tyr Asn Glu Lys
 1               5                  10                  15

Asn Met Phe Tyr Ser Ser Ser Gln Asp Phe Ser Ser Cys Glu Asp Ser
             20                  25                  30

Ser Gln Phe Ala Asp Asp Ser Gly Phe Phe Asp Asp Ser Glu Ile Ser
         35                  40                  45

Ser Ile Gly Tyr Glu Ile Gly Ser Lys Leu Ala Ala Met Cys Asp Asp
     50                  55                  60

Phe Asp Ala Gln Met Met Ser Tyr Ser Ala His Ala Ser Asp Arg Ser
 65                  70                  75                  80

Leu Phe His Arg Leu Leu Asp Phe Phe Ala Phe
                 85                  90
```

EGL-1, A NEW PROTEIN REQUIRED FOR PROGRAMMED CELL DEATH IN *C. ELEGANS* THAT INTERACTS WITH THE BCL-2-LIKE PROTEIN CED-9

CROSS REFERENCE TO RELATED APPLICATIONS

This application claims priority from U.S. provisional Ser. No. 60/047,836, filed May 28, 1997; and filed Ser. No. 60/085,541 May 15, 1998.

BACKGROUND OF THE INVENTION

The field of the invention is cell death.

Programmed cell death is a physiological process that has been conserved through evolution (Ellis, Ann. Rev. Cell Biol. 7:663–698, 1991; Raff, Nature 356:397–400, 1992). Genetic analyses of the cell-death process in *C. elegans* have defined a genetic pathway for programmed cell death (reviewed by Horvitz et al., Cold Spring Harbor Symposia on Quantitative Biology LIX, 377–385, 1994). Mutations in three genes, ced-9, ced-4, and ced-3 (ced, cell death abnormal), affect, most if not all, of the 131 somatic cell deaths that occur during the development of the *C. elegans* hermaphrodite (Sulston and Horvitz, Dev. Biol. 56:110–156, 1977; Sulston et al., Dev. Biol. 100:64–119, 1983). Loss-of-function (lf) mutations in ced-3 or ced-4 result in the survival of cells that normally die, indicating that these genes are required for the killing process (Ellis and Horvitz, Cell:44:817–829, 1986). ced-9, by contrast, is a negative regulator of programmed cell death. A gain-of-function (gf) mutation in ced-9 prevents most if not all programmed cell deaths, and loss-of-function (lf) mutations in ced-9 cause embryonic lethality as a consequence of ectopic cell death (Hengartner et al., Nature 356:494–499, 1992). This lethality is suppressed by loss-of-function mutations in ced-3 or ced-4, indicating that ced-3 and ced-4 act downstream of, or in parallel to, ced-9 (Hengartner et al., Nature 356:494–499, 1992). ced-4 is likely to act upstream of ced-3, since cell death induced by ced-4 overexpression is greatly reduced in the absence of ced-3 activity (Shaham and Horvitz, Genes Dev. 10:578–591, 1996). The ced-9, ced-4, and ced-3 central cell-death machinery is thought to be regulated by cell-type-specific regulators, which includes the cell-death specification genes ces-1 and ces-2; these two genes specify the life-versus-death decisions of a subset of cells, including the sisters of the NSM neurons in the pharynx (Ellis and Horvitz, Development 112:591–603, 1991).

The genetically established interactions among ced-9, ced-4, and ced-3 may reflect direct physical interactions of the protein products of these genes. The CED-9 protein binds to the CED-4 protein (Spector et al., Nature 385:653–656, 1997; Chinnaiyan et al., Science 275:1122–1126, 1997; Wu et al., Science 275:1126–1129, 1997; James et al., Curr. Biol. 7:246–252, 1997; Ottilie et al., Cell Death and Differentiation 4:526–533, 1997), which, in turn, can bind to the CED-3 protein (Chinnaiyan et al., Science 275:1122–1126, 1997; Wu et al., J. Biol. Chem. 272:21449–21454,1997). Furthermore, the interaction of CED-4 with CED-3 appears to lead to the activation of CED-3 and the initiation of cell death (Seshagiri and Miller, Curr. Biol. 7:455–460, 1997; Chinnaiyan et al., Nature 388:728–729, 1997; Wu et al., J. Biol. Chem. 272:21449–21454,1997).

ced-9 and ced-3 have mammalian counterparts also shown to be involved in programmed cell death. ced-9 encodes a protein structurally and functionally similar to the mammalian cell-death inhibitor Bcl-2 (Hengartner and Horvitz, Cell 76:665–676, 1994), the prototype of a family of Bcl-2-like molecules that act as regulators of cell death in mammals (reviewed by White, Genes Dev. 10:1–15, 1996; Rinkenberger and Korsmeyer, Curr. Op. Gen. Dev. 7:589–596, 1997). CED-3 is a member of a family of invertebrate and mammalian cysteine proteases, collectively called caspases, that are cell-death effectors acting mainly downstream of Bcl-2-like cell-death regulators (reviewed by Fraser and Evan, Cell 85:781–784, 1996; Nicholson and Thornberry, Trends Biochem. Sci. 22:299–306, 1997).

Recently, a new group of mammalian cell-death activators has been identified. These proteins, which include Bik, Bid, Harakiri, and Bad, interact with Bcl-2-like proteins and can induce cell death when overexpressed (Yang et al., Cell 80:285–291, 1995; Boyd et al. Oncogene 11:1921–1928, 1995; Han et al., Mol. Cell. Biol. 16:5857–5864, 1996; Wang et al., 1996; Inohara et al., EMBO J. 16:1686–1694, 1997; Zha et al., J. Biol. Chem. 272:24101–24104, 1997; Kelekar et al., Mol. Cell. Biol. 17:7040–7046, 1997; Ottilie et al., J. Biol. Chem. 272:30866–30872, 1997). The amino acid sequences of these cell-death activators are dissimilar, except for a nine amino acid stretch similar to one of the four Bcl-2 homology (BH) domains, the BH3 domain, and particularly similar to the BH3 domain of the Bcl-2-like cell-death activators Bax and Bak (Chittenden et al., EMBO J. 14:5589–5596, 1995; 1995; Han et al., Genes Dev. 10:461–477,1996 1996b; Zha et al., J. Biol. Chem. 271:7440–7444, 1996; Hunter and Parslow, J. Biol. Chem. 271:8521–8524, 1996). As in the cases of Bax and Bak (Chittenden et al., EMBO J. 14:5589–5596, 1995; Han et al., Genes Dev. 10:461–477,1996), the BH3 domains of this new group of cell-death activators are important both for their interaction with Bcl-2-like molecules and for their ability to induce cell death (Wang et al., Genes Dev. 10:2859–2869, 1996; Inohara et al., EMBO J. 16:1686–1694, 1997; Zha et al., J. Biol. Chem. 272:24101–24104, 1997; Kelekar et al., Mol. Cell. Biol. 17:7040–7046, 1997; Ottilie et al., J. Biol. Chem. 272:30866–30872, 1997).

It would be useful to identify and clone additional genes in the *C. elegans* cell death pathways. Due to the conservation between nematode and mammalian cell death pathways, identification of such genes and their encoded proteins could allow detection of therapeutic targets, therapeutic compounds, and novel cell death genes.

SUMMARY OF THE INVENTION

We have discovered and cloned a new *C. elegans* cell death gene, egl-1 (egl, egg-laying defective) that encodes a protein that interacts with CED-9 and that contains a region similar to the BH3 domains of BH3-containing cell-death activators. Gain-of-function mutations in egl-1, such as egl-1(n1084 n3082), cause the two HSN neurons, which are required for egg laying, to inappropriately undergo programmed cell death; these mutants were identified in screens for egg-laying defective (Egl) mutations (Trent et al., Genetics 104:619–647, 1983). By isolating a dominant suppressor of the egl-1 Egl phenotype, we identified a loss-of-function mutation in the egl-1 gene, egl-1(n1084 n3082). This mutation prevents not only the ectopic deaths of the HSNs but most if not all normally occurring programmed cell deaths, indicating that egl-1 is a cell-death activator and encodes a component of the general cell-death machinery in *C. elegans*.

In the first aspect, the invention features substantially pure nucleic acid encoding EGL-1 polypeptide. Such nucleic acid is defined by its ability to complement any of the egl-1 (n1084 n3082) mutations provided herein or by the ability to suppress mutations in egl-1(n1084). Preferably, specifically excluded is the exact wild-type nucleic acid sequence provided at the ced(n3082) map position in the *C. elegans* Genome Consortium database on May 28, 1997; conservative substitutions of this sequence are, however, preferably included. In a related aspect, the invention features egl-1 nucleic acids which have deletions. Fusions of additional nucleic acids to the egl-1 gene are also included, as are fragments sufficient for use as primers, probes, or synthesis of epitopes for antibody preparation. Homologs of *C. elegans* egl-1 from other species (and fragments, fusions, deletions, and other mutations therein) are also a related aspect of the invention. Homologs are defined as having at least 50%, preferably 90% identity over at least 100 base pairs, or as being able to complement at least one egl-1 (n1084 n3082) allele and having at least 20% identity over the entire gene. Identity is preferably determined using the Sequence Analysis Software Package of the Genetics Computer Group, University of Wisconsin Biotechnology Center, Madison, Wis. 53705, on the default settings.

In a related aspect the invention provides polypeptide encoded by the egl-1 gene. Proteins encoded by egl-1 nucleic acids which are fragmented, deleted or fused to other sequences are also included. For example, the BH3 domain (and nucleic acids encoding the same).

In another aspect, the invention features an antibody which specifically binds a protein encoded by the egl-1 gene. By "specifically binds" is meant capable of binding with a kd of at least 10–8M.

In another aspect, the invention features a nematode having a mutation in the egl-1 gene. Preferably, the mutation is genetically engineered or is a suppressor of the egl-1 Egl phenotype.

In yet another aspect, the invention features a method for identifying a compound or gene which affects cell death, said method comprising exposing a nematode having either a egl-1(n1084 n3082) or other egl-1 mutation to the compound or nucleic acid and looking for amelioration of the phenotype caused by the gene. In a related aspect the invention features a method of identifying novel cell death genes or alleles by looking for genetic suppressors of either egl-1 mutations or mutations which are egl-1(n1084 n3082)-like mutations mapping within a map unit of egl-1.

In yet other aspects of the invention, methods for detecting proteins which interact with EGL-1 and methods for purifying non-*C. elegans* homologs of EGF-1 are also provided.

By "modulating cell death" or "altering cell death" is meant increasing or decreasing the number of cells which undergo programmed cell death in a given cell population. Preferably, the cell population is selected from a group including T-cells, neuronal cells, fibroblasts, or any other cell line known to undergo apoptosis in a laboratory setting (e.g., the baculovirus infected insect cells). It will be appreciated that the degree of modulation provided by an EGL-1 polypeptide or modulating compound in a given assay will vary, but that one can determine the statistically significant change in the level of cell death which identifies an EGL-1 polypeptide or a compound which modulates the egl-1 gene or the EGL-1 polypeptide.

By "inhibiting cell death" is meant any decrease in the number of cells which undergo programmed cell death relative to an untreated control. Preferably, the decrease is at least 25%, more preferably the decrease is 50%, and most preferably the decrease is at least one-fold.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably over the entire nucleotide sequence of the referenced sequence.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By a "substantially pure polypeptide" is meant an EGL-1 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, EGL-1 polypeptide. A substantially pure EGL-1 polypeptide may be obtained, for example, by extraction from a natural source (e.g., a fibroblast, neuronal cell, or lymphocyte cell); by expression of a recombinant nucleic acid encoding an EGL-1 polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure nucleic acid" is meant nucleic acid that is free of the genes which, in the naturally-occurring genome of the organism from which the nucleic acid of the invention is derived, flank the gene. The term therefore includes, for example, a recombinant nucleic acid which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. Further included are RNA molecules encoded by egl-1 and nucleic acid sequences which are antisense.

By "transformed cell" is meant a cell into which (or into an ancestor of which) has been introduced, by means of recombinant DNA techniques, a DNA molecule encoding (as used herein) an EGL-1 polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic nematodes or mammals (e.g., rodents such as rats or mice) and the DNA (transgene) is inserted by artifice into the nuclear genome or by an extrachromosomal array.

By "transformation" is meant any method for introducing foreign molecules into a cell. Microinjection, lipofection, calcium phosphate precipitation, retroviral deliver, electroporation and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fingi, algae, animal tissue, and cultured cells.

By "positioned for expression" is meant that the DNA molecule is positioned adjacent to a DNA sequence which directs transcription and translation of the sequence (i.e., facilitates the production of, e.g., an EGL-1 polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "conserved region" is meant any stretch of six or more contiguous amino acids exhibiting at least 30%, preferably 50%, and most preferably 70% amino acid sequence identity to EGL-1.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}$P or $^{35}$S) and nonradioactive labelling (e.g., chemiluminescent labelling, e.g., fluorescein labelling).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an EGL-1 specific antibody. A purified antibody may be obtained, for example, by affinity chromatography using recombinantly-produced protein or conserved motif peptides and standard techniques.

By "specifically binds" is meant an antibody which recognizes and binds a protein but which does not substantially recognize and bind other molecules in a sample, e.g., a biological sample, which naturally includes protein.

Other features and advantages of the invention will be apparent from the following description of the preferred embodiments thereof, and from the claims.

BRIEF DESCRIPTION OF THE DRAWINGS

FIG. 3 shows phenotype scoring indicating that n3082 suppresses the egl-1(n1084) phenotype by suppressing the death of the HSNS.

FIG. 4 shows n3082 suppressed the death of not only the HSNS, but most (if not all) cells normally undergoing programmed cell death.

FIG. 7 shows the predicated Egl-1 nucleic acid and protein sequences (SEQ ID NO:1 and SEQ ID NO:2, respectively.

FIGS. 8A and 8B shows the sequences of the complete egl-1 transcript and protein product. Amino acids underlined (58 to 64) constitute the BH3-like region. The five nucleotides deleted by the n3082 mutation are indicated by the horizontal bar. FIG. 8B shows alignment of the EGL-1 BH3-like region with the BH3 domains of BH3-containing proteins (human Bik, accession number U34584; mouse Bid, U75506; human Harakiri, U76376; and mouse Bad, L37296) and the Bcl-2-like proteins Bak and Bax (human Bak, U23765; human Bax, L22474). Amino acids that are identical in at least four of the seven sequences and conserved amino acids are shaded in dark and light grey, respectively.

FIG. 11 is a diagram showing egl-1(n1084 n3082) does not suppress the lethality caused by ced-9 (lf) mutations.

FIG. 12 is a diagram of genetic data showing egl-1(n1084 n3082) acts at least partly through ced-9.

FIG. 13 is a diagram of genetic data showing that egl-1 (n1082 n3082) can suppress a ces-1 (lf) mutation.

FIG. 17A is a diagram showing the genetic pathway for programmed cell death in C. elegans. egl-1 appears to act between the cell-death specification gene ces-1 and the anti-cell-death gene ced-9. FIG. 17B is a diagram showing the molecular model for the role of EGL-1 in initiating programmed cell death. EGL-1 displaces CED-4 from the membrane-bound cell-death inhibitor CED-9, thereby allowing CED-4 to trigger downstream events required for the killing process. FIG. 18 is a diagram showing that expression of the egl-1 cDNA under control of a heat shock promoter can rescue the Ced phenotype of egl-1(n1O84 n3082) animals.

DETAILED DESCRIPTION

I. Characterization of egl-1 and EGL-1

Figure 1:
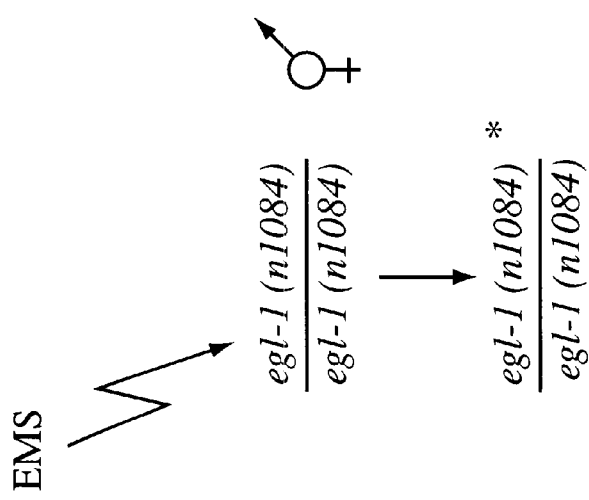
FIG. 1 is a schematic of the genetic screen used to identify loss-of-function (lf) mutations in egl-1.
Figure 2:
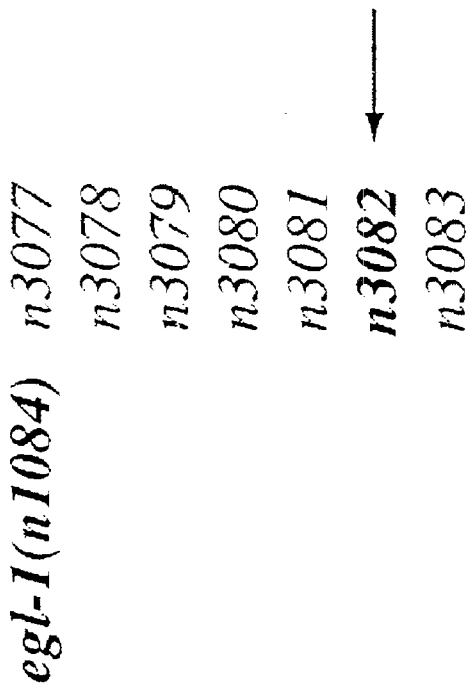
FIG. 2 shows seven mutations, including n3082, which can revert the egl-1 gain-of-function (gf) phenotype.

Identification of egl-1(n1084 n3082) We analyzed the gene egl-1(egl, egg-laying abnormal), which has previously only been defined by gain-of-function (gf) mutations and whose gf phenotype suggests a possible role in cell-death specification. Hermaphrodites carrying egl-1 (gf) mutations are egg laying defective (Egl) because the hermaphrodite-specific neurons (HSNs), which are required for proper egg-laying, undergo programmed cell death (Desai et al., Genetics 121:703–721, 1989; Trent et al., Genetics 104:619–647, 1983). In an attempt to isolate loss-of-function (lf) mutations in egl-1 , we performed a screen for suppressors of the Egl-1(gD) phenotype and isolated a group of seven allelic mutations (FIGS. 1 and 2). These suppressor mutations prevent not only the death of the HSNs in egl-1 (gf) hermaphrodites, but also most, if not all, of the 131 programmed cell deaths that normally occur during C. elegans development (FIGS. 3 and 4). Thus, like the ced-9 (gf) mutation and lf mutations in ced-3 and ced-4, mutations in this suppressor gene block programmed cell death. This cell-death abnormal (Ced) phenotype is recessive, and we have used it to map one of the seven suppressor mutations, n3082, very close to the region of chromosome V to which egl-1 was earlier localized (Desai et al., Genetics 121:703–721, 1989; Trent et al., Genetics 104:619–647, 1983). Specifically, n3082 maps to LGV between him-5 and unc-112, just to the right of egl-1(n1084). No gene known to be able to mutate to cause a cell death defect has previously been mapped to this region, although animals homozygous for a deficiency uncovering this locus are cell death defective. These results suggest that the suppressor mutations are lf mutations in a new cell death gene, ced(n3082).

Identification of ced(n3082) as egl-1

The suppressor mutation n3082 is a loss-of-function mutation in the egl-1 gene. We have determined that the that n3082 is allelic to the egl-1 (gf) mutations (described below).

Cloning and Molecular Characterization

Figure 5:
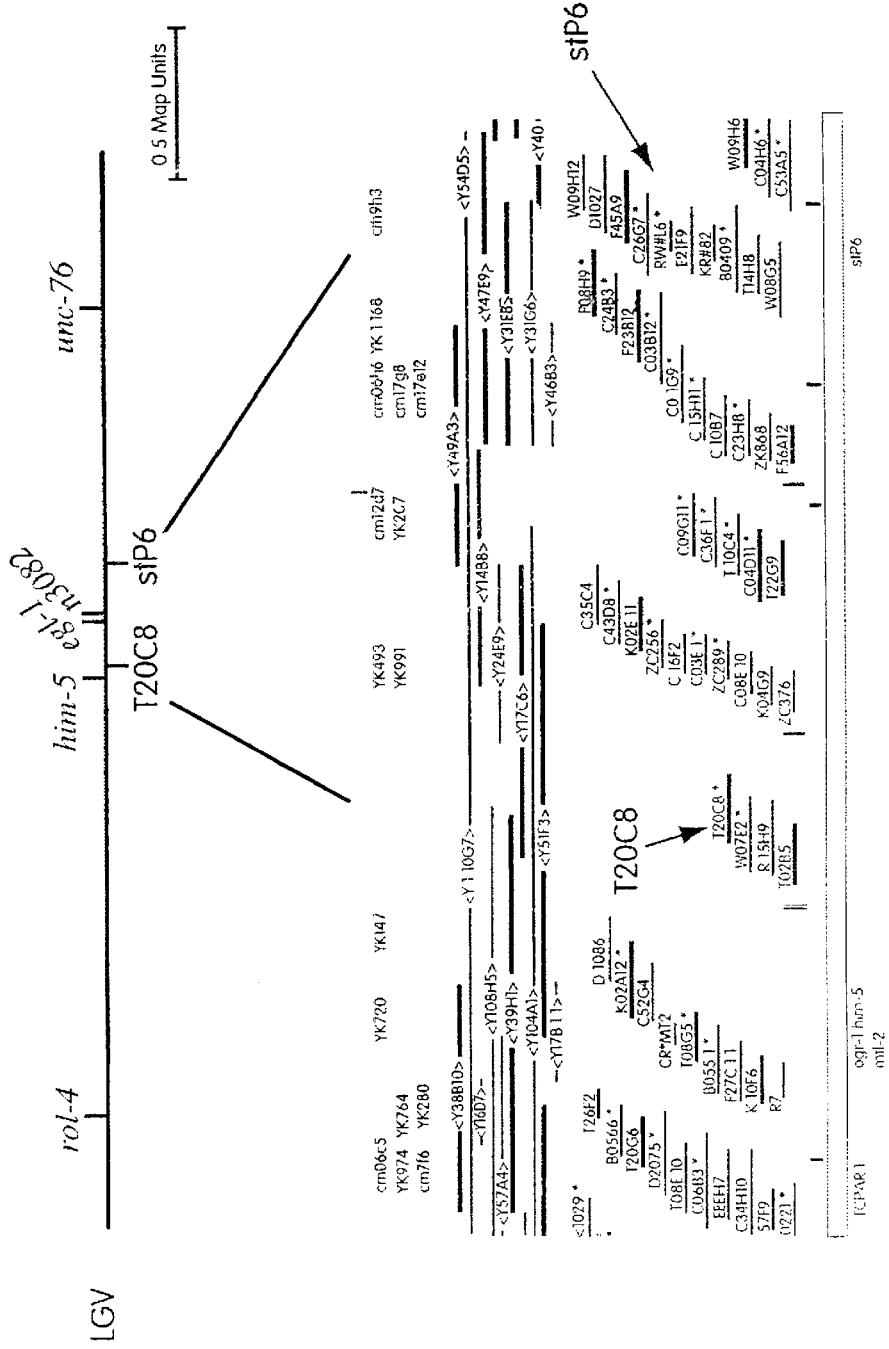
FIG. 5 is a schematic showing the mapping of n3082.
Figure 6:
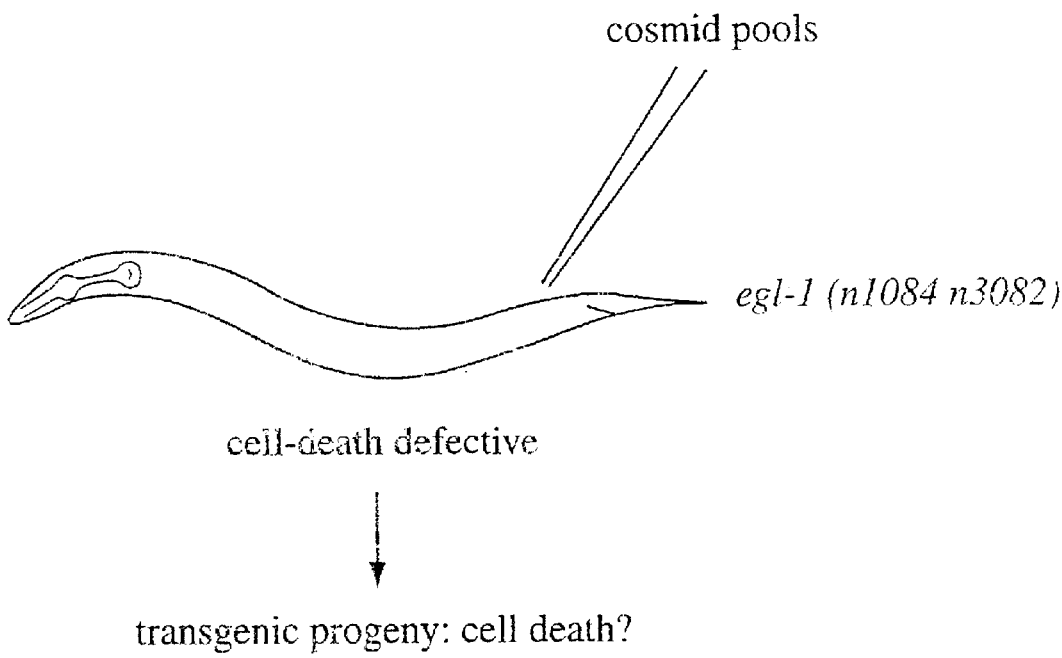
FIG. 6 is a diagram of transformation rescue of the n3082 Ced phenotype.

Using RFLP mapping and transformation rescue, we have identified a genomic fragment which can rescue the Ced phenotype of n3082 (FIGS. 5 and 6). This fragment lies in a region of the C. elegans genome which has been sequenced by the C. elegans genome consortium. Whereas the version of Genefinder (the program used to predict coding sequences and genes) used by the genome consortium does not predict any genes on this fragment, our version predicts one transcription unit composed of two exons that could encode a novel protein of 91 amino acids (FIG. 7).

The EGL-1 protein is overall a novel protein but we have identified a stretch of 9 amino acids in the center of EGL-1 that are similar to the Bcl-2 homology region 3 called BH3 domain (reviewed by Rinkelberger and Korsmeyer, Curr. Op. Gen. Dev. 7:589–596, 1997; FIGS. 8A and 8B). The EGL-1 protein is therefore similar in structure to a recently defined group of mammalian cell death activators, the BH3-only containing proteins (Yang et al., Cell 80:285–291, 1995; Boyd et al., Oncogene 11:1921–1928, 1995; Han et al., Mol. Cell. Biol. 16:5857–5864, 1996a; Wang et al., Genes Dev. 10:2859–2869, 1996; Inohara et al., Embo. J. 16:1686–1694, 1997; Zha et al., J. Biol. Chem. 272:24101–24104, 1997; Kelekar et al., Mol. Cell. Biol. 17:7040–7046, 1997; Ottilie et al., J. Biol. Chem. 272:30866–30872, 1997). These proteins can induce cell death when overexpressed in mammalian cells but their physiological significance has not been determined yet.

Frameshift mutations introduced into exon 1 confirm that the identified transcription unit confers rescuing activity. Using the minimal rescuing fragment as a probe, we have isolated a cDNA which can rescue the Ced phenotype of n3082 when expressed using a C. elegans heat shock promoter. In addition, DNA sequence changes in each of the seven suppressors are located in the coding region of this gene, suggesting that we have cloned the gene responsible for the Ced phenotype and for the suppression of the Egl-1(gf) phenotype. The DNA lesion found in all seven suppressors is an identical 5 bp deletion at the beginning of exon 2. This deletion is predicted to result in the generation of a truncated protein composed of the first half of the wild-type protein (44 AA) and a 16 AA abnormal C-terminal extension.

Figure 9:
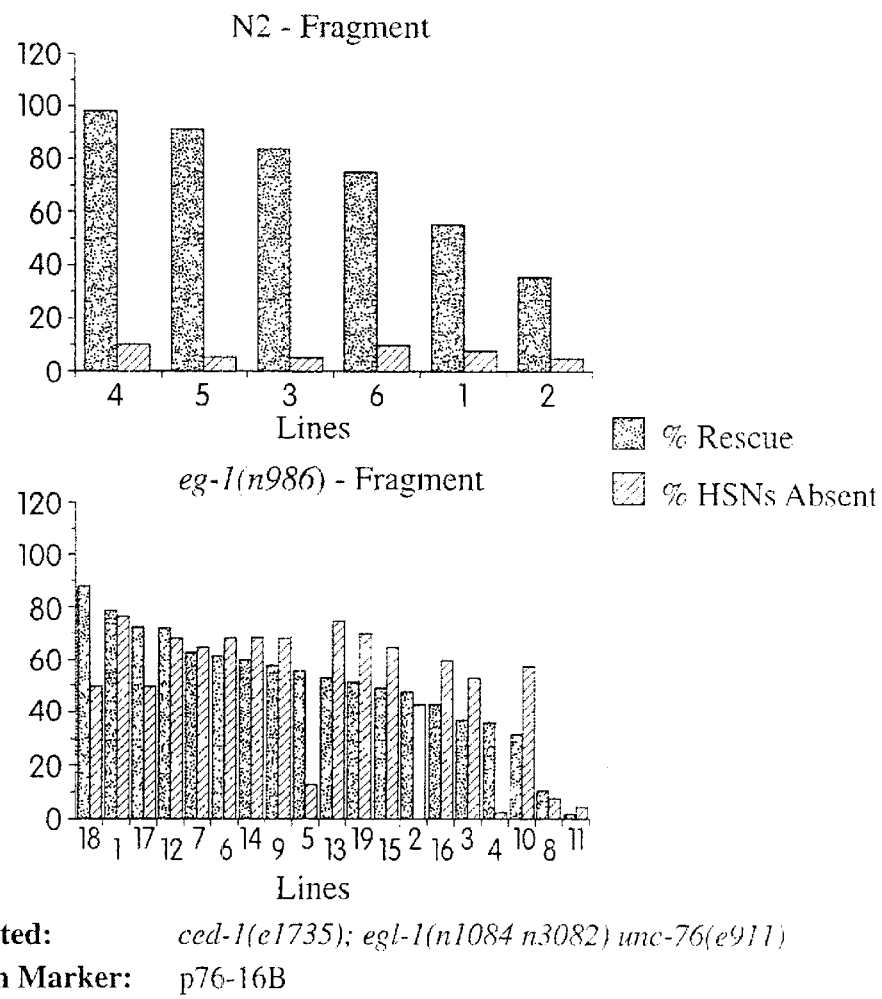
FIG. 9 is a diagram showing that an 8 kb PCR-fragment which includes the the egl-1 gene and 6 kb of its downstream region can phenocopy the Egl-1 (gf) phenotype when amplified from egl-1 (gf) animals.
Figure 10:
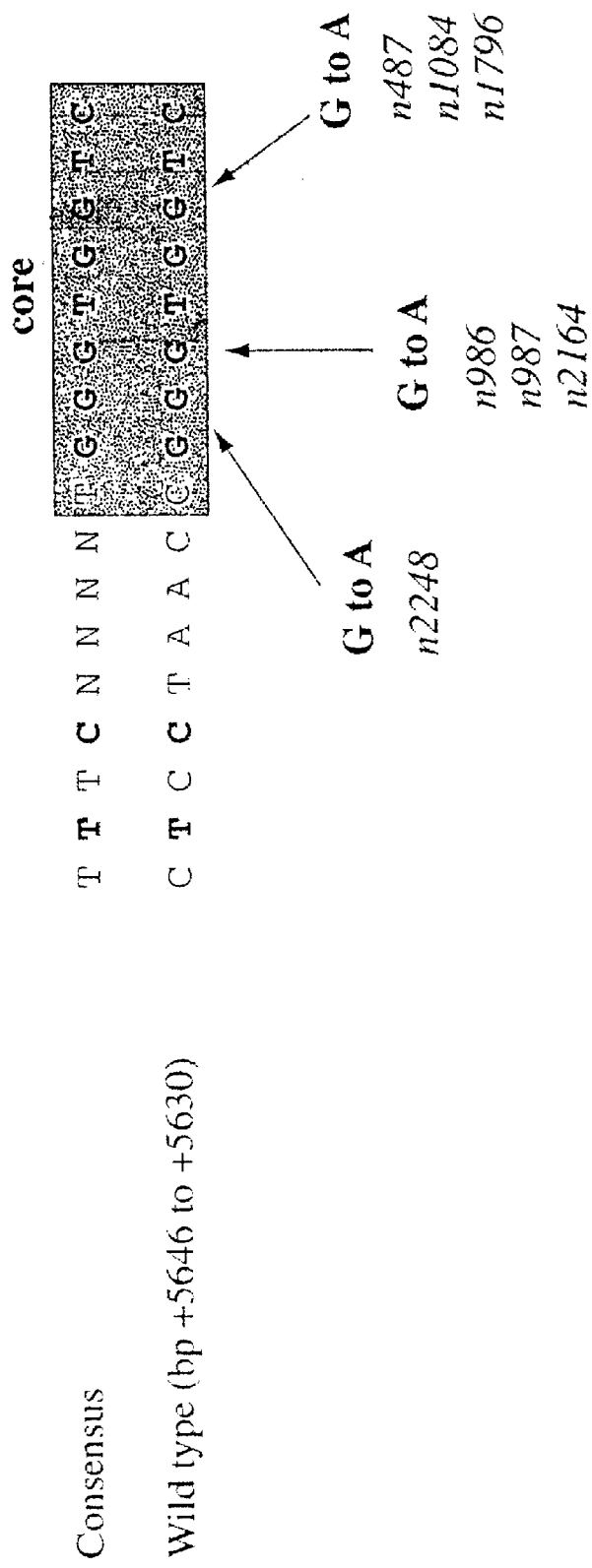
FIG. 10 is a diagram showing that egl-1 (gf) mutations disrupt a putative TRA-1 DNA binding site.
Figure 14:
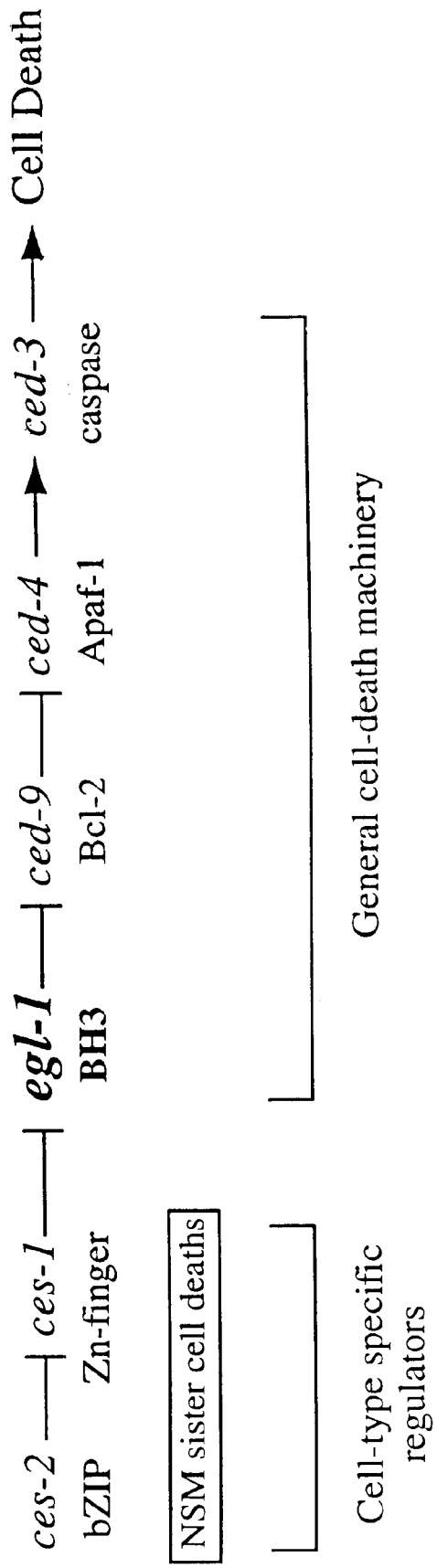
FIG. 14 is a diagram showing that egl-1 represents a new component of the general cell death machinery, acting downstream of the cell-death specification genes and upstream of ced-9.
Figure 15:
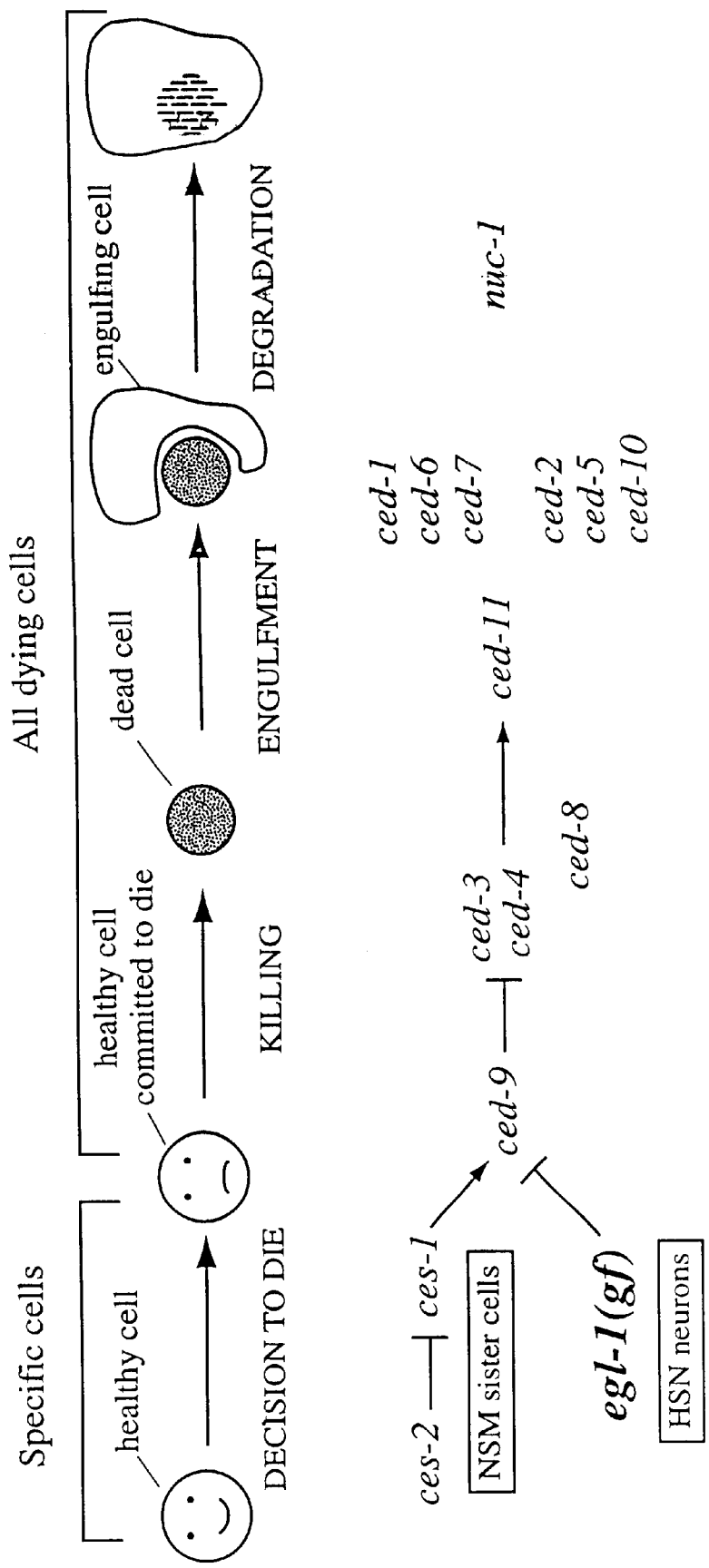
FIG. 15 is a diagram showing the genetic pathway of programmed cell death in *C. elegans*.

The egl-1(gf) mutations affect 3' regulatory regions of the egl-1 gene. Using a functional assay which was based on the observation that an 8 kb PCR-fragment covering the egl-1 gene and 6 kb of its downstream region were sufficient to phenocopy the egl-1(gf) phenotype (egg-laying defective) (see FIG. 9, we have identified the egl-1(gf) mutations. The seven egl-1(gf) mutations are single base changes within a stretch of five bases 5.6 kb downstream of the egl-1 open reading frame (FIG. 10). These mutations are required in cis to a functional egl-1 gene in order to cause the egl-1(gf) phenotype which suggests that they affect the transcriptional regulation of the egl-1 gene. The egl-1(gf) mutations are in a sequence motif that is reminiscent of the DNA-binding domain of TRA-1, the terminal, global regulator of somatic sex-determination in *C. elegans* (Zarkower and Hodgkin, Cell 70:237–249, 1992).

Genetic Analyses

To determine where in the cell death pathway egl-1 acts, we have analyzed whether egl-1(n1084 n3082) can suppress the ced-9(lf) phenotype (FIG. 11). In contrast to ced-3(lf) and ced-4(lf) mutations, egl-1(n1084 n3082) does not suppress the lethality caused by a ced-9(lf) mutation, indicating that it acts upstream of or in parallel to ced-9. Data further suggest that egl-1 requires the presence of the wild-type ced-9 gene for normal function, which indicates that it acts at least partly through ced-9 and possibly by negatively regulating ced-9 (FIG. 12). Finally, egl-1(n1084 n3082) can suppress a lf mutation in ces-1, indicating that egl-1 acts downstream of or in parallel to ces-2 and ces-1, the genes involved in cell death specification (FIG. 13).

In summary, with the isolation and characterization of a suppressor of the egl-1(gf) phenotype, we have identified a new ced gene, egl-1, which encodes for a novel protein. egl-1 appears to be required for programmed cell death at a point possibly downstream of the cell-death-specification genes and upstream of ced-9.

Functional Analyses

Genetically, the egl-1 gene is necessary for programmed cell death in *C. elegans*. To determine whether the egl-1 gene is also sufficient to induce cell death, we used the cell-type specific *C. elegans* mec-7 promoter ($P_{mec-7}$) to ectopically express the egl-1 cDNA in the ALM touch receptor cells which normally survive. The expression of egl-1 in these cells resulted in the death of 90% of these neurons, suggesting that the EGL-1 protein is sufficient to kill (see Table 1). The egl-1-induced killing was blocked by mutations in ced-9, ced-4, and ced-3, indicating that egl-1-induced killing was killing by programmed cell death.

Figure 16A:
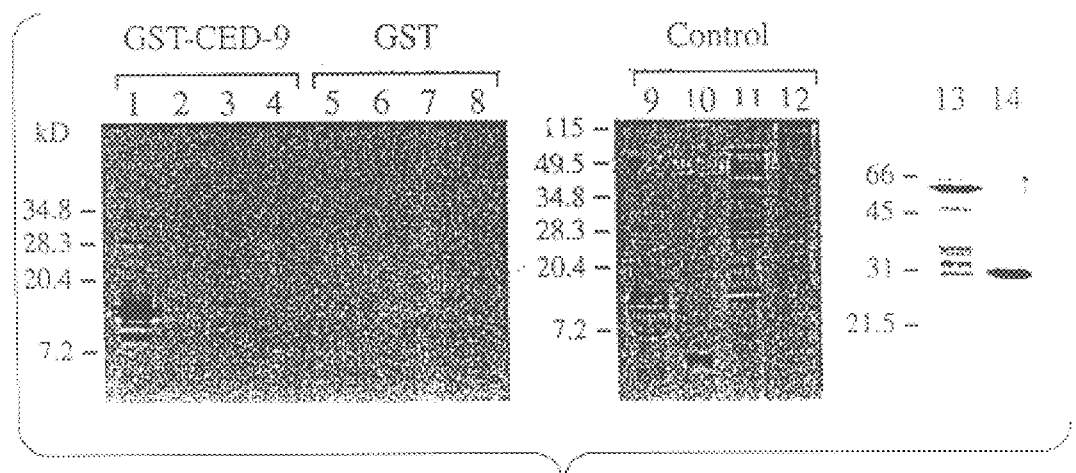
FIG. 16A is a picture of a gel showing wild-type CED-9 and EGL-1 proteins interact in vitro. $^{35}$S-labeled S.TAG-EGL-1 (lanes 1 and 5; 14.5 kD), S.TAG alone (lanes 2 and 6; 6.7 kD), luciferase (lanes 3 and 7; 61 kD), or SSN6 (lanes 4 and 8; 107 kD) were incubated with GST-CED-9 (lanes 1–4; 60 kD) or GST alone (lanes 5–8; 27 kD) and analyzed for binding by SDS-PAGE and autoradiography, as described in Experimental procedures. Lanes 9–12 represent 10% of the input of S.TAG-EGL-1 (lane 9), S-TAG (lane 10), luciferase (lane 11), and SSN6 (lane 12). Lanes 13 and 14 represent 60% of GST and 40% of GST-CED-9 protein used per binding reaction (12% SDS-PAGE, stained with Commassie blue).
Figure 16B:
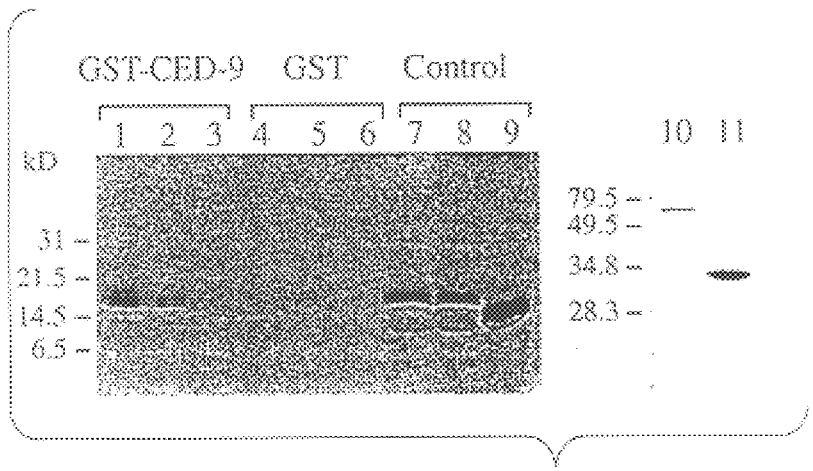
FIG. 16B is a picture of a gel showing that the interaction between CED-9 and EGL-1 depends on the BH3-like region of EGL-1. $^{35}$S-labeled S.TAG-EGL-1 (lanes 1, 4), S.TAG-EGL-1 with a deletion of the BH3-like region (S.tag-EGL-1 ΔBH3) lanes 2, 5; 13.4 kD) or S.TAG-EGL-1 protein encoded by the egl-1(n1084 n3082) allele (which causes a frameshift and premature termination) (S.TAG-EGL-1 trunc) (lanes 3, 6; 11.2 kD) were incubated with GST-CED-9 (lanes 1–3) or GST alone (lanes 4–6) and analyzed for binding. Lanes 7–9 represent 10% of the input of S.TAG-EGL-1 (lane 7), S.TAG-EGL-1 ΔBH3 (lane 8), or STAG-EGL-1 trunc (lane 9). 40% of the GST-CED-9 and GST proteins are shown in lanes 10 and 11(15% SDS-PAGE, stained with Coomassie blue).
Figure 17A:
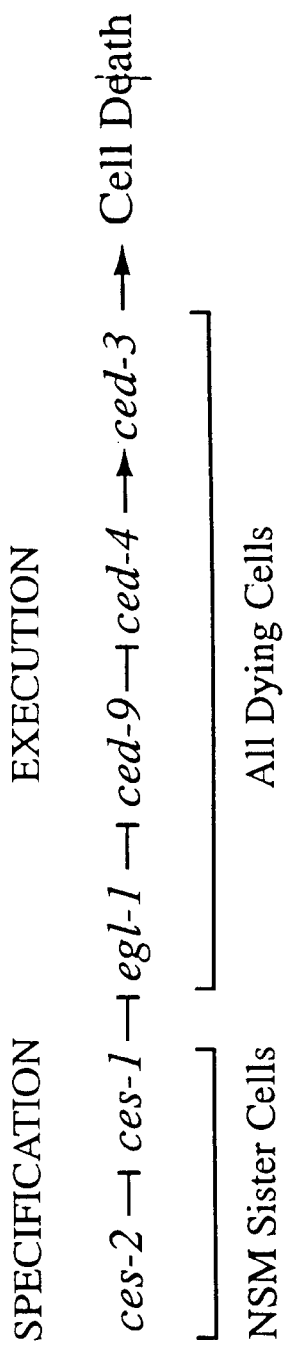
FIGS. 17A and 17B show the function of egl-1 in programmed cell death in C. elegans.
Figure 17B:
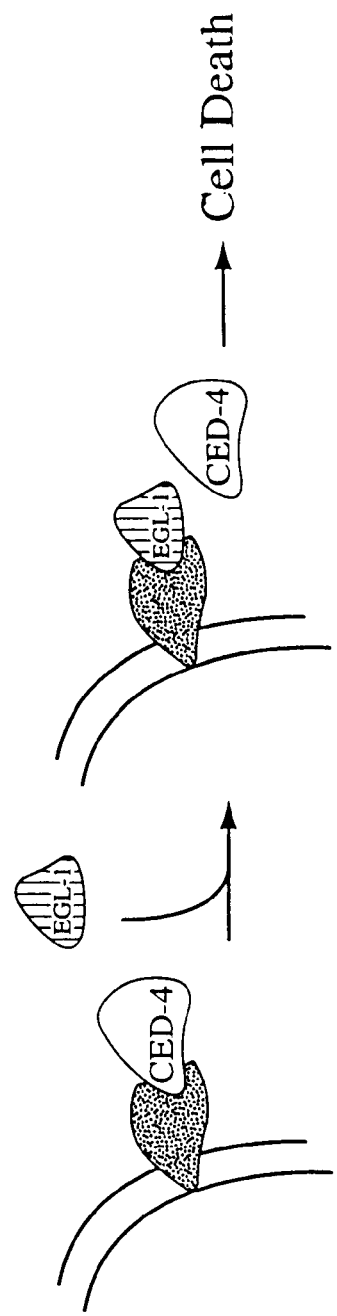

As described under "Genetic Analyses", the egl-1 gene might be a negative regulator of ced-9 which encodes a Bcl-2-like cell death inhibitor. The EGL-1 protein is similar in structure to the family of mammalian BH3-only containing cell death activators. These molecules are thought to activate cell death by binding to Bcl-2-like cell death inhibitors. Using a yeast two-hybrid system and glutathione-S-transferase pull-down experiments, we have now determined that the *C. elegans* CED-9 and EGL-1 proteins interact (see FIG. 16A and 16B). We propose that the EGL-1 protein activates cell death by binding to thereby negatively regulating the CED-9 protein (see FIG. 17).

TABLE 1 egl-1-Induced Ectopic Killing is Suppressed by Mutations that Block Programmed Cell Death

| Transgene | % ALMs Surviving (n = 60) |
| --- | --- |
| $P_{mec-7}$A | 98 |
| $P_{mec-7}$B | 100 |
| $P_{mec-7}$egl-1 A | 8 |
| $P_{mec-7}$egl-1 B | 9 |
| $P_{mec-7}$egl-1 C | 10 |
| $P_{mec-7}$egl-1 C/+ | 50 |
| $P_{mec-7}$egl-1 C; ced-9 (gf) | 98 |
| $P_{mec-7}$egl-1 C; ced-4 (lf) | 97 |
| $P_{mec-7}$egl-1 C; ced-3 (lf) | 98 |

Transgenic animals were generated and ALMs in transgenic L1 larvae scored as described in Experimental Procedures. Control lines $P_{mec-7}$ A and B contained extrachromosomal arrays of $P_{mec-7}$ and experimental lines contained $P_{mec-7}$ egl-1 A-C integrated arrays of the transgene $P_{mec-7}$ egl-1. Mutations used were as follows: ced-9 (gf) was ced-9 (n 1950), ced-4 (lf) was ced-4 (n1162), and ced-3 (lf) was ced-3(n717).

II. Identification of Mammalian Homologs

The basic cell death machinery has been conserved from *C. elegans* to mammals. The EGL-1 protein is similar in structure to the mammalian BH3-only containing cell death activators. In addition, both, the EGL-1 protein as well as the mammalian BH3-only containing proteins, can induce cell death when ectopically expressed and interact with Bcl-2-like cell death inhibitors. EGL-1 and the mammalian BH3-only containing proteins might therefore be functional homologues. To test this, we have tested whether the EGL-1 protein can bind to the human Bcl-2 protein. Data suggest that, using a yeast two-hybrid system, EGL-1 interacts with human Bcl-2. This result supports the hypothesis that EGL-1 and mammalian BH3-only containing proteins are functionally homologous. In addition, it indicates that the process of programmed cell death is evolutionarily conserved even upstream of bcl-2/ced-9.

The fact that BH3-only containing proteins and EGL-1 are functionally similar or even homologous does not mean that there is not a true mammalian EGL-1 sequence homologue, e.g., a homologue that shares sequence identity with EGL-1 throughout the length of the protein. One may therefore utilize egl-1 nucleic acids to identify a sequence homologue in other organisms using approaches described in the art. One can, for example, search the available nucleotide, protein, and EST databases for sequences with homology to egl-1. In addition, one can use various more sophisticated programs, such as structural algorithms, to look for egl-1-related proteins.

In addition to the above, another approach to defining additional functionally important regions of a *C. elegans* protein is to clone and sequence its homologs from related Caenorhabditis species, such as *C. briggsae* and *C. vulgaris* (Shaham et al., Cell 86:201–208, 1996), or, if necessary, from more distantly related species. Domains of the gene that are required for function are expected to be conserved among the three species (e.g., the BH-3 domain and domains conserved within nematodes). The conserved regions may be used to design degenerate oligonucleotide primers for the identification of mammalian homologues using PCR amplification and mammalian cDNAs as templates.

To characterize the encoded protein one may generate antibodies against the EGL-1 protein. They may be tested for their ability to recognize homologous mammalian proteins.

As described under "Functional Analyses", we have determined that the EGL-1 protein can interact with the *C. elegans* CED-9 protein in a yeast two-hybrid system and also in vitro. In addition, EGL-1 can interact with the mammalian homologue of CED-9, Bcl-2, in yeast. One may thus also use the two-hybrid system to identify other structural and functional Egl-1 homologues.

III. Identification of Novel Genes and Compounds that can Block Programmed Cell Death in *C. elegans*

When expressed under the control of a *C. elegans* heat shock promoter, the egl-1 cDNA can not only rescue the cell death defect caused by the n3082 mutation but can also induce ectopic cell death resulting in lethality (FIG. 18). This phenomenon can be employed to search for novel genes required for programmed cell death and for compounds that can block programmed cell death. To this end, an extrachromosomal array carrying the egl-1 cDNA (or an equivalent) under the control of a *C. elegans* heat shock promoter (or an equivalent) may be integrated into the *C. elegans* genome to generate lines which stably inherited the construct. The percent of heat shock-induced lethality in such lines is expected to be 100%. To identify genes required for cell death, one may then search for mutations that can suppress the heat shock-induced lethality. Such mutations can define a variety of genes needed for programmed cell death, including direct and indirect targets of egl-1, and regulators of egl-1 activity. Likewise, to test whether certain drugs or other compounds can block programmed cell death, one can assay to determine whether they are able to block the egl-1(n3082)-induced lethality (or the equivalent). This approach can be modified to a high-throughput format for drug screening, for example using microtiter wells and automated procedures. Such screening should identify small molecules that inhibit the EGL-1 protein as well as those that inhibit upstream regulators and downstream targets of EGL-1.

Other Embodiments

In other embodiments, the invention includes any protein which is substantially identical to an EGL-1 polypeptides; such homologs include other substantially pure naturally-occurring EGL-1 proteins, as well as allelic variants; natural mutants; induced mutants; DNA sequences which encode proteins and also hybridize to the egl-1 DNA sequences provided herein under high stringency conditions or, less preferably, under low stringency conditions (e.g., washing at 2×SSC at 40° C. with a probe length of at least 40 nucleotides); and proteins specifically bound by antisera directed to a EGL-1 polypeptide. The term also includes chimeric polypeptides that include a EGL-1 portion. Specifically, excluded are the mammalian BH-3-containing polypeptides and nucleic acid sequences known in the art and listed herein above under the heading "Cloning and Molecular Characterization).

The invention further includes analogs of any naturally-occurring EGL-1 polypeptide. Analogs can differ from the naturally-occurring EGL-1 protein by amino acid sequence differences, by post-translational modifications, or by both. Analogs of the invention will generally exhibit at least 85%, more preferably 90%, and most preferably 95% or even 99% identity with all or part of a naturally-occurring EGL-1 amino acid sequence provided herein. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring EGL-1 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-1 length polypeptides, the invention also includes EGL-1 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of EGL-1 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a EGL-1 nucleic acid or amino acid sequence in a sample to be diagnosed.

All publications and patent applications mentioned in this specification are herein incorporated by reference to the same extent as if each independent publication or patent application was specifically and individually indicated to be incorporated by reference.

What is claimed is:

1. A purified Egg-Laying defective-1 (EGL-1) polypeptide which alters the commitment of a cell to cell death by binding to a Bcl-2 or CED-9 polypeptide, said EGL-1 polypeptide comprising a BH-3 domain having amino acid residues 58–66 of SEQ ID NO: 2 and having an amino acid sequence at least 50% identical to SEQ ID NO: 2.

2. The polypeptide of claim 1, comprising an amino acid sequence having at least 85% sequence identity to SEQ ID NO: 2.

3. The polypeptide of claim 2, comprising an amino acid sequence having at least 90% sequence identity to SEQ ID NO: 2.

4. The polypeptide of claim 3, comprising an amino acid sequence having at least 95% sequence identity to SEQ ID NO: 2.

5. The polypeptide of claim 4, comprising an amino acid sequence having at least 99% sequence identity to SEQ ID NO: 2.

6. A purified EGL-1 polypeptide which alters the commitment of a cell to cell death by binding to a Bcl-2 or CED-9 polypeptide, said polypeptide comprising the amino acid sequence of SEQ ID NO:2.

7. A therapeutic composition comprising as an active ingredient the EGL-1 polypeptide of any one of claim 1, 2, 3, 4, 5, or 6, said active ingredient being formulated in a physiologically acceptable carrier.

8. A method for detecting a compound that binds to an EgL-1 polypeptide which alters the commitment of a cell to cell death by binding to a Bcl-2 or CED-9 polypeptide, said EGL-1 polypeptide comprising a BH-3 domain having amino acid residues 58–66 of SEQ ID NO: 2 and an amino acid sequence at least 50% identical to SEQ ID NO: 2, said method comprising the steps of:

contacting under suitable conditions an EGL-1 polypeptide, or fragment thereof, with a candidate compound; and detecting the binding of said compound to said EGL-1 polypeptide or fragment thereof, wherein said binding indicates that said compound is involved in the increase of apoptosis.

9. The method of claim 8, wherein said compound is a polypeptide.

10. The method of claim 8, wherein said EGL-1 polypeptide comprises a sequence 85% identical to SEQ ID NO: 2.

11. The method of claim 10, wherein said EGL-1 polypeptide comprises a sequence 90% identical to SEQ ID NO: 2.

12. The method of claim 11, wherein said EGL-1 polypeptide comprises a sequence 95% identical to SEQ ID NO: 2.

13. The method of claim 12, wherein said EGL-1 polypeptide comprises a sequence 99% identical to SEQ ID NO: 2.

14. The method of claim 13, wherein said EGL-1 polypeptide comprises the amino acid sequence of SEQ ID NO: 2.

15. A method for detecting a compound that binds to an EGL-1 polypeptide which alters the commitment of a cell to cell death by binding to a Bcl-2 or CED-9 polypeptide, said EGL-1 polypeptide comprising a BH-3 domain having amino acid residues 58–66 of SEQ ID NO: 2 and an amino acid sequence at least 50% identical to SEQ ID NO: 2, said method comprising the steps of:

contacting under suitable conditions an EGL-1 polypeptide, or fragment thereof, with a candidate compound; and detecting the binding of said compound to said EGL-1 polypeptide or fragment thereof, wherein said binding indicates that said compound is involved in the decrease of apoptosis.

* * * * *

UNITED STATES PATENT AND TRADEMARK OFFICE
CERTIFICATE OF CORRECTION

PATENT NO. : 6,596,495 B1
APPLICATION NO. : 09/087137
DATED : July 22, 2003
INVENTOR(S) : Horvitz et al.

Page 1 of 1

It is certified that error appears in the above-identified patent and that said Letters Patent is hereby corrected as shown below:

<u>Column 5,</u>
Line 32, "fingi" should be -- fungi --.

<u>Column 7,</u>
Line 13, "Commassie blue" should be -- Coomassie blue --.

<u>Column 9,</u>
Line 2, "reminescent" should be -- reminiscent --.

Signed and Sealed this

Twenty-seventh Day of June, 2006

JON W. DUDAS
*Director of the United States Patent and Trademark Office*